Figure 2:
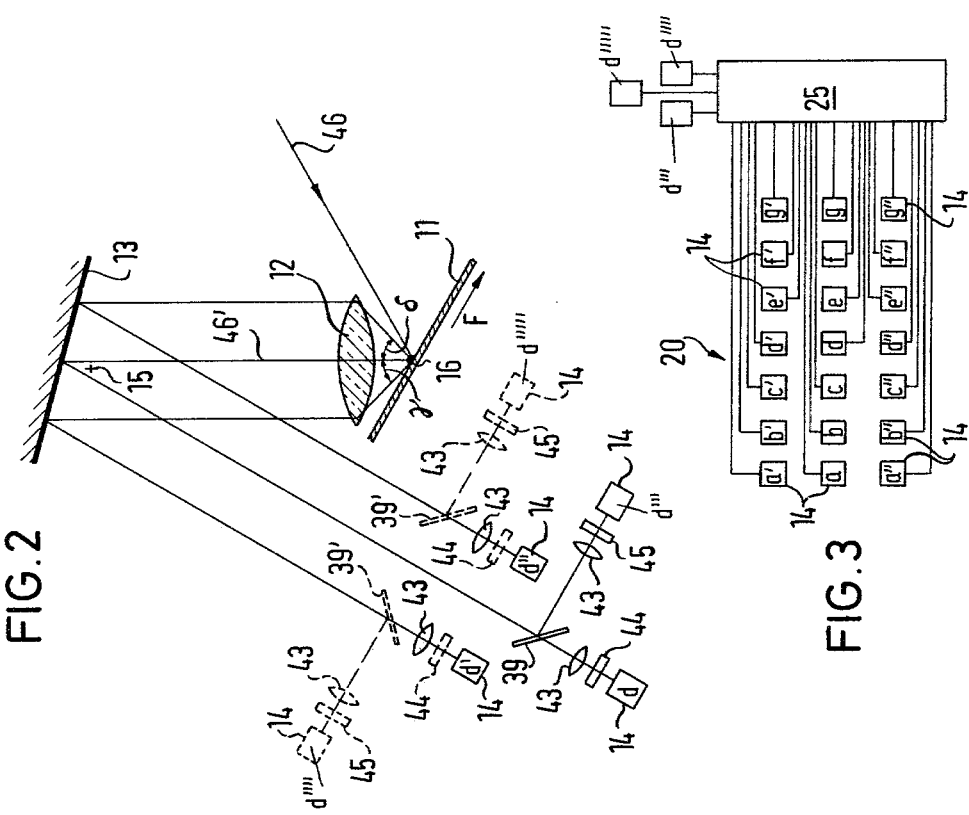

United States Patent [19]

Sick

[11] 4,306,813
[45] * Dec. 22, 1981

[54] APPARATUS FOR DETERMINING FAULTS IN STRIP MATERIAL

[75] Inventor: Erwin Sick, Icking, Fed. Rep. of Germany

[73] Assignee: Erwin Sick GmbH, Optik-Elektronik, Fed. Rep. of Germany

[*] Notice: The portion of the term of this patent subsequent to Feb. 3, 1998, has been disclaimed.

[21] Appl. No.: 49,366

[22] Filed: Jun. 18, 1979

Related U.S. Application Data

[63] Continuation-in-part of Ser. No. 972,301, Dec. 22, 1978, Pat. No. 4,248,537.

[30] Foreign Application Priority Data

Jun. 23, 1978 [DE] Fed. Rep. of Germany ....... 2827704

[51] Int. Cl.³ .................... G01N 21/32; G01B 11/30
[52] U.S. Cl. .................................. 356/431; 250/572; 356/407
[58] Field of Search ............... 356/429, 430, 431, 238, 356/407; 250/563, 572

[56] References Cited

U.S. PATENT DOCUMENTS 3,198,951  8/1965  Lentze ............................. 250/563

3,922,090 11/1975 Fain ..................................... 356/407
3,984,189 10/1976 Seki et al. ........................... 356/431
4,004,152  1/1977 Obser et al. ........................ 356/431
4,172,666 10/1979 Clark ................................. 356/431

Primary Examiner—R. A. Rosenberger
Attorney, Agent, or Firm—Townsend and Townsend

[57] ABSTRACT

Apparatus for determining faults in strip material is disclosed in this application which enables both color defects and distortions of the surface of the strip material to be recognized.

It its general form the apparatus illuminates the material surface at a specific angle with white light and an optical system directs the light leaving the surface to a number of photodetection devices which detect the various angles at which light leaves the surface. The deviations of these angles from the direction of specular reflection, or unimpeded transmission, are characteristic of the nature of the distortion of the surface of the strip material. At least the photodetection device which receives the specularly reflected or normally transmitted light and preferably all the photodetection devices, includes two photodetectors, which detect light in different spectral ranges by means of associated beam splitting and filtering devices. In this way color defects such as stains or spots on the surface can also be recognized.

6 Claims, 8 Drawing Figures

APPARATUS FOR DETERMINING FAULTS IN STRIP MATERIAL

This invention relates to an apparatus for determining faults on strip material and is a continuation in part of my earlier copending application U.S. Ser. No. 972,301, filed Dec. 22, 1978, entitled "Optical Apparatus for determining the light exit angle from a material strip illuminated by a light beam", now U.S. Pat. No. 4,248,537, issued Feb. 3, 1981.

In this earlier application there is described and claimed an arrangement in which a strip of material is scanned linewise by a light bead and angular deflections or deviations produced in the light reflected from, or transmitted through, the strip of material are detected to provide an indication of the presence and the nature of a fault.

In one embodiment the light leaving the material surface is collected by a cylindrical lens extending parallel to the line scanned by the light bead and is directed to a strip-like cylindrically concave mirror with its focal line at right angles to the line scanned by the light bead. In this way a physical separation of the light beams leaving the surface of the strip at different angles is produced in the image plane of the cylindrical mirror and can be detected by an array of photodetectors. The arrangement, which is characterised by its inherent simplicity of construction and its efficiency, is principally intended to detect physical imperfections such as dents, depressions and scratches in the material surface which are characterised by the different angular deviations they produce in light from the scanning light bead.

The present invention has as one of its objects the provision, in an apparatus as described in the earlier application, of the facility of recognising not only the aforementioned defects but also defects of colour such as spots or stains.

It is a further object of the present application to also provide apparatus capable of recognising defects such as bumps, dents or scratches which in addition are miscoloured.

It is a yet further object of the present application to provide optical fault detecting apparatus which is endowed with the ability to recognize colour defects, and defects which manifest themselves by spectrally affecting incident light.

The light detection systems of the aforementioned earlier application are based on photodetectors either arranged in an array in the image field of the cylindrical mirror or disposed at the end faces of light conducting rods themselves strategically disposed to receive light from the image field of the cylindrical mirror. Both these light detection systems are also suitable, in modified form for use for the purposes of the present application.

The present invention is thus particularly concerned with a further development of the apparatus of patent application Ser. No. 972,301. The use of the present invention is not however of necessity restricted to use with the apparatus of the earlier application.

The present invention thus relates in particular to the determination of faults which deflect a sharply defined non-monochromatic light beam incident at a predetermined angle through predetermined angular amounts, e.g. in a specific range of solid angles. The non-monochromatic light beam should contain as many different spectral ranges as practicable and is preferably a white light beam.

Whilst previously known apparatuses of this kind mostly work with monochromatic laser light it is significant in relation to the present invention that light is used which contains at least two different spectral ranges.

Apparatus for determining faults in this way and in particular for differentiating between different kinds of faults must thus be able to distinguish between light rays, or light beams, which leave a surface at different angles. The invention can be used with special advantage in apparatus for determining surface faults in sheet metal. In this connection the light beam is directed obliquely onto the sheet metal and the receiving cylindrical lens is preferably arranged at the angle of reflection. The apparatus can, however, also be used as a transmission device in particular for surveying foils or textiles and in this connection the receiving cylindrical lens is preferably located in an extension of the sharply defined light beam which impinges on the strip (or web) from one side. Faults in the strip then result in characteristic angular deflections and/or scattering of the light beam into solid angular ranges corresponding to the nature of the fault.

The determination of scratches on metal surfaces and also large area bumps or dents on the surface is of especial importance. In each case, however, the fault determining apparatus of the invention usefully has an additional receiving channel which operates by remission which in known manner responds to defects (stains or spots) which influence the remitted light. A detection channel of this kind can also be provided to the side of the main beam for the recognition of defects when illuminating foils by transmitted light. This channel can operate both with remitted light and also with scattered transmitted light. For textiles an additional defect recognition channel of this kind operates in remission.

In addition to the aforementioned earlier application other apparatus is also already known for detecting the angles at which light leaves a surface.

Thus optical apparatus has already become known from DE-AS No. 25 32 603 for the detection of light leaving the surface of a strip at different angles. This apparatus, however, requires a light conducting rod of rectangular cross-section and of higher optical quality as the light conduction in the light conducting rod must be so exactly carried out that the original angular relation between the light beams leaving the scanning bead and passing to the detector are fully preserved.

A significantly lower optical quality can be accepted for the light conducting rod if this is not used to differentiate between the different angles at which light leaves a surface but rather is only used to pass light sent in another manner from a specified angular range onto its surface by total reflection to a photodetector arranged at one or both end faces of the light conducting rod. An apparatus of this kind for monitoring a material strip for the location of faults is known from DE-OS No. 24 33 683. This known apparatus, however, only makes it possible to distinguish between two angular ranges lying in a specified plane.

A completely new type of light conducting rod has become known from DE-OS No. 25 08 366, this light conducting rod is provided at its side diametrically opposite to the light entry surface region with a narrow stepped mirror arrangement which extends in a straight line in the direction of the longitudinal axis of the rod and the individual mirrors of the stepped mirror arrangement are inclined to the longitudinal axis of the light conducting rod in such a way that diametrically incident light is deflected at angles of total reflection into the light conducting rod. It is important in this connection that the light rays extending in a section at right angles to the optical axis do not fall at normal incidence but rather at oblique incidence onto the small plane mirrors in order that after a single or multiple total reflection, the light rays so far as possible do not impinge for a second time on the stepped mirror arrangement where they would be lost from the further light conduction.

The previously known light conducting rod is of round cross-section and makes it possible to guide the largest part of the received light incident on the surface region to a photodetector provided at one or both end faces. If only one photodetector is arranged at one end face the opposite end face of the light conduction rod is usefully made reflecting. It is also already known to form the individual mirrors of the stepped mirror arrangement with convex curvature transversely to the longitudinal axis in order to improve the scattering effect which improves the homogeneity. Furthermore, several very narrow stepped mirror arrangements can be arranged directly alongside one another.

The new light conducting rod which results in a significantly larger light yield is e.g. used in an optical scanning system, e.g. for investigating a strip of material, in accordance with DE-OS No. 25 50 815, of course in this case a differentiation between different angular ranges of the light leaving the material strip is not possible.

In accordance with an older suggestion for an apparatus for detecting the location of faults on the reflecting surface of a web three light conducting rods, of the type known among other things from DE-OS No. 25 08 366, are arranged in parallel alongside one another so that the central light conducting rod is somewhat displaced in the direction of the light beam relative to the two side disposed light conducting rods. By means of suitably arranged cylindrical lenses the light leaving the surface of the web at different angular ranges is respectively deflected onto only one of the three light conducting rods. The central light conducting rod receives the light leaving the strip at the angle of reflection whilst the two side disposed light conducting rods work in the dark region.

According to a generalised form of the present invention there is provided an apparatus for determining faults in strip material comprising illuminating means for illuminating the strip material at a predetermined angle, means for transmitting light from at least one of the angular ranges at which light leaves the material surface to associated detection means and wherein said detection means comprises at least first and second detectors, means for passing a portion of said light which contains at least two spectral ranges to each of the first and second detectors and associated filter means whereby each of said first and second detectors detects light in different spectral ranges.

If it is simply desired to detect e.g. stains or spots on the surface of the material which do not affect the angle of specular reflection or transmission from the surface but solely the spectral content of the light then it is sufficient to carry out the spectral analysis at a central photodetection means which normally receives the specularly reflected or normally transmitted beam.

In accordance with an aspect of the present invention which is based on the apparatus of the earlier application there is provided apparatus for determining faults on strip material with a light deflecting device illuminated by a light beam to form a scanning light bead on the strip, a cylindrical lens extending over the scanning region and having a focal line extending along the scanning track of the scanning light bead on the strip, a strip-like cylindrical mirror arranged behind the cylindrical lens and spaced therefrom with its focal line extending optically at right angles to the direction of scanning movement of the scanning light bead, and a light receiving device with at least two photodetectors arranged in the focal plane of the cylindrical mirror the photodetectors receiving light from light beams which leave the strip in different angular ranges and one of which receives light leaving the strip at the angle of reflection, the apparatus being characterised in that, by means of filtering, only light in a first spectral range is transmitted to the one central photodetector and at least a portion of the beam transmitted to this photodetector is branched off prior to filtering and, after the filtering out of a second spectral range, is passed to a further photodetector.

The central photodetector is thus usefully located at that central region of the light receiving device where the light would impinge for an exactly reflecting surface, if necessary taking into account the unavoidable trivial tilting that can occur during transport of the strip. The light beam incident on the relevant photodetectors can also be designated as "the main light" as the light which impinges in this channel corresponds to a strip surface undisturbed by other than colour faults and defects. Preferably, in accordance with the invention, two colour channels, e.g. for red and blue are used and this already allows a more certain recognition of faulty colouring of the surface.

In an apparatus with at least one photodetector arranged to the side of the central photodetector and receiving the light beams deflected transversely to the scanning direction, the invention envisages that this photodetector also receives filtered light and that at least a portion of the light beam directed to the photodetector is branched off prior to filtering and, after the filtering out of a second spectral range, is passed to a further photodetector.

This embodiment also makes it possible to recognize colour faults in the vicinity of dent-like depressions or bumps on the surface of the strip.

In connection with the embodiment of the earlier application which utilizes light conducting rods the invention envisages that the one central light conducting rod which is covered at its central region where the light would impinge with an exactly specularly reflecting surface, if necessary taking into account the unavoidable trivial tilting that can occur during transport of the strip, is covered by a stop which is impervious to light.

In this connection the stop is preferably a deflecting mirror. In this way the central light conducting rod, which is preferably surrounded by two side disposed light conducting rods serves to recognize scratches in the dark field. The main light is kept away from the light conducting rod by the said stop.

An especially preferred embodiment for the recognition of colour faults on the surface of the strip is characterized in that the deflected light beam is divided, in accordance with its wave length, into at least two partial beams and that each partial beam is passed to a photodetector. The preferred colours here are also the two colour channels red and blue.

For that embodiment of the apparatus in accordance with the earlier application which utilizes a deflecting mirror arranged in the central region of the side disposed light conducting rod or rods the invention envisages that the deflected light beam or beams is or are split by wave length into at least two partial beams and that each partial beam is passed to a respective photodetector.

This embodiment likewise allows the recognition of coloured dent-like depressions or bumps on the surface of the strip.

Figure 3:
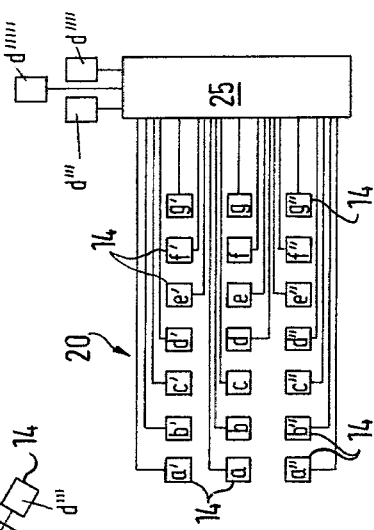
Figure 1:
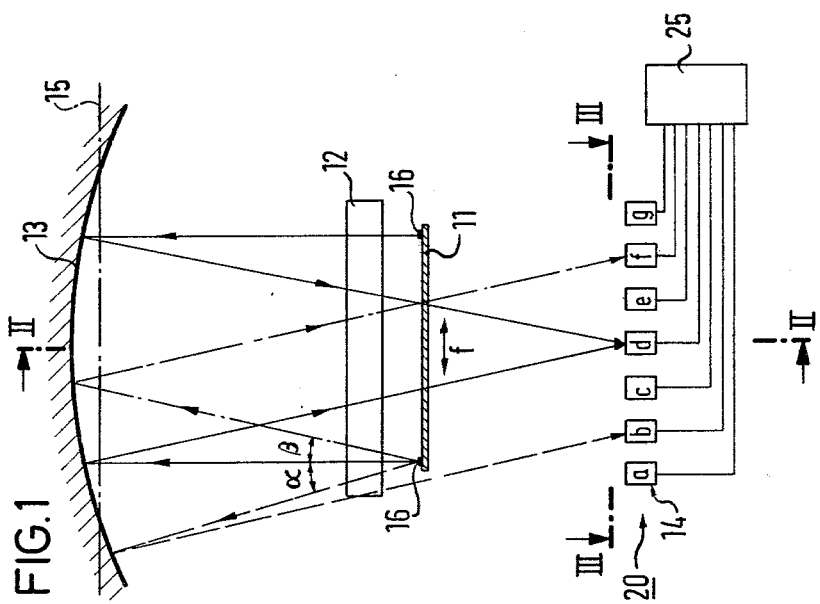
Figure 4:
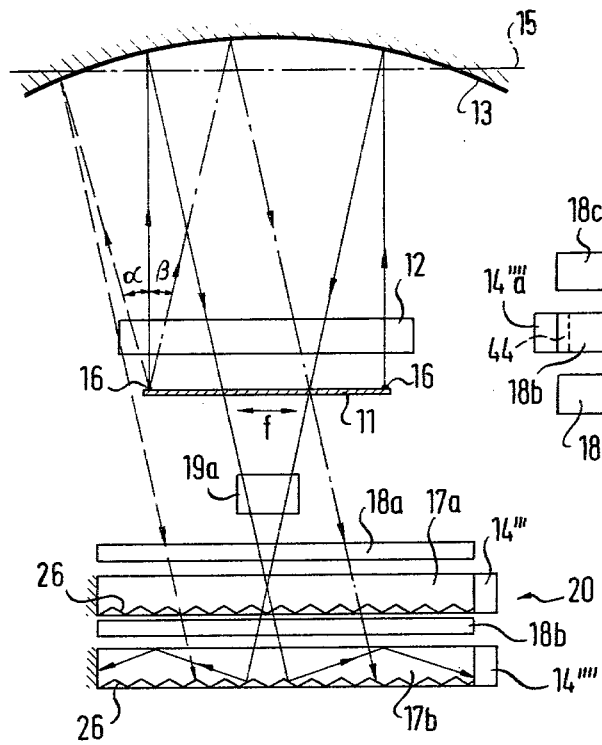
Figure 6:
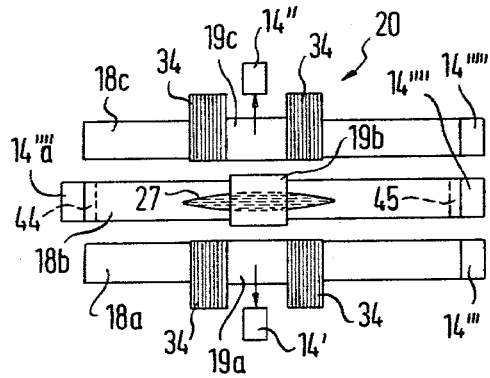
Figure 5:
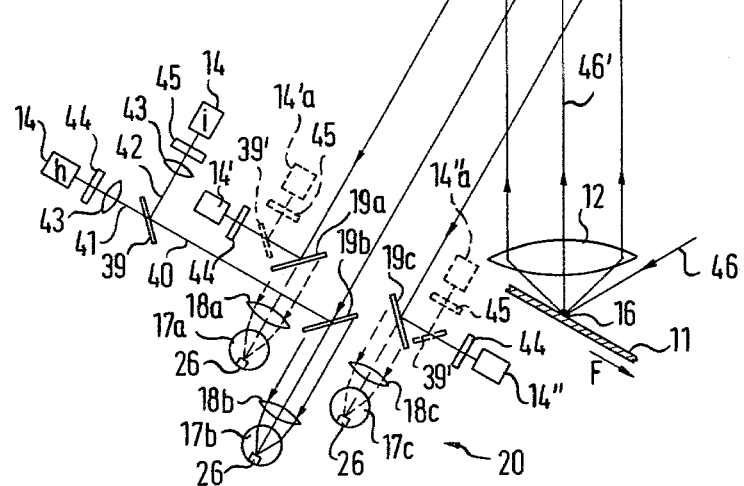
Figure 7:
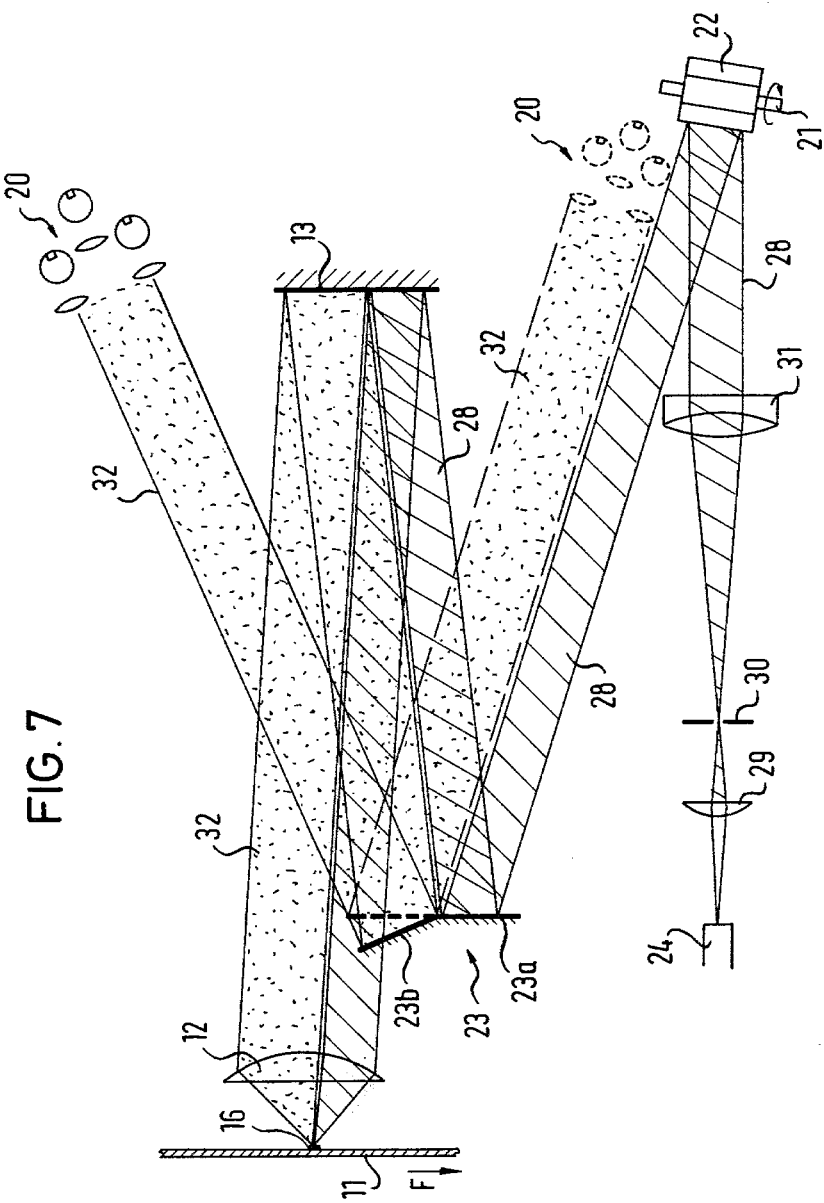
Figure 8:
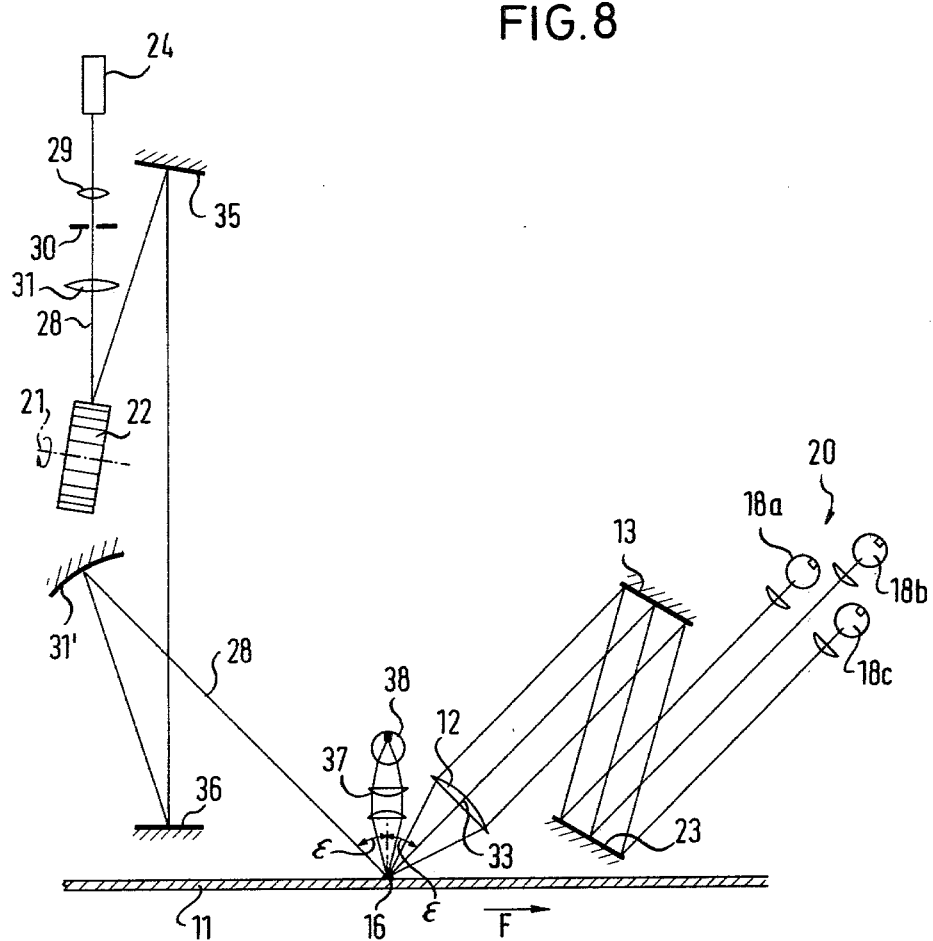

The invention will now be described by way of example in the following and with reference to the drawings in which are shown:

FIG. 1 a schematic side elevation of a preferred embodiment of the optical apparatus for determining the light exit angle, FIG. 2 a view on the line II—II of FIG. 1, FIG. 3 a view on the line III—III of FIG. 1, FIG. 4 a view of a further advantageous embodiment analogous to FIG. 1, FIG. 5 a view of the embodiment of FIG. 4 analogous to the view of FIG. 2, FIG. 6 a view of the embodiment of FIG. 4 analogous to the view of FIG. 3, FIG. 7 a schematic view of a further embodiment of the optical apparatus in accordance with the invention in which some optical elements are used both for the transmitted and received beam path and FIG. 8 a schematic view analogous to FIGS. 2 and 5 of a further especially advantageous embodiment.

As seen in FIGS. 1 to 3 a sheet metal strip 11 moves in the direction of the arrow F in continuous fashion. It can e.g. represent a sheet metal strip 11 leaving a rolling mill. In the view of FIG. 1 the direction of movement F of the strip is inclined to the plane of the drawing.

A small light bead 16 generated by a scanning ray 46 at oblique incidence and displaced parallel to itself periodically scans the material strip 11 over its entire width in the direction of the double arrow f of FIG. 1. The scanning beam 46 can e.g. be generated by the embodiment of FIG. 7 using a wide strip light source 24 and via a mirror wheel 22 and a concave mirror 13. The scanning velocity and the velocity of the strip are so related one to the other that, taking into account the spatial extent of the small light bead 16 the entire surface of the material strip 11 is sequentially detected by the scanning light bead 16.

A cylindrical lens 12 extends parallel to the material strip 11 and its spacing from the scanning head 16 on the material strip 11 is equal to its focal length. The focal line of the cylindrical lens 12 is disposed at the location of the scanning light bead 16. The focal line thus substantially coincides with the line described by the scanning light bead 16. A cylindrical mirror 13 is arranged at a significantly larger distance from the strip 11 than the cylindrical lens 12 and the axis of the cylindrical mirror is at right angles to the axis of the cylindrical lens 12. The cylindrical mirror 13 has an elongate strip form; its longitudinal axis is designated 15. The longitudinal axis 15 of the cylindrical mirror 13 extends parallel to the material strip 11 and to the axis of the cylindrical lens 12.

As seen in FIG. 2 the cylindrical mirror 13 is so tilted about its longitudinal axis 15 from its position parallel to the cylindrical lens 12 that in accordance with FIG. 2 all the light beams embraced by the cylindrical lens 12 are then deflected past the cylindrical lens 12 to a receiving device 20 which is spaced from the cylindrical mirror 13 by its focal length and which comprises, in the embodiment of FIGS. 1 to 3 a matrix arrangement of photodetectors 14a, 14b, 14c, . . . ; 14a', 14b', 14c', . . . ; 14a'', 14b'', 14c'', . . . The photodetectors are all connected via a respective line to an electronic processing circuit 25 in which the detected signals are connected together in a desired manner.

As seen in FIG. 1 all the light leaving the material strip 11 at the angle of reflection is united at the central photodetector 14d. As the light bead 16 at a specified time only covers a specified point on the surface of the material strip 11 the incidence of light on the photodetector 14d shows that light from the light bead 16 leaves at the angle of reflection.

In FIG. 1 the light bead 16 is e.g. shown at two points on the surface of the material strip 11. In reality the light bead 16 does not, however, reach both points simultaneously but rather at sequential times.

It is e.g. assumed in FIG. 1 that in addition two further light beams leave the light bead 16 illustrated at the left of the drawing at angles $\alpha$ and $\beta$ to the normal. These beams impinge, on account of the arrangement of the invention on the photodetectors 14b and 14f and, indeed, independently of the specific point on the material strip 11 at which the scanning bead 16 is located.

FIG. 2 shows that different light exit angles in the plane at right angles to FIG. 1 also result in the light impinging on different photodetectors. Whilst the light beam leaving the material strip 11 at the angle of reflection in FIG. 2 impinges, as in FIG. 1, on the central photodetector 14d, the beams assumed e.g. to be scattered at the angles $\gamma$ and $\delta$ reach the neighbouring photodetectors 14d' and 14d''.

Should the deflections in both planes be superimposed e.g. the deflection $\alpha$ in FIG. 1 and the deflection $\gamma$ of FIG. 2 then the received light falls on further photodetectors of the matrix arrangement of FIG. 3, in the above assumed example on the photodetector 14b'.

In this manner it is also possible, depending on the resolution of the matrix arrangement to distinguish between different spatial ranges in which the light leaves the scanning light bead 16 and, indeed, independently from the actual position of the scanning cycle at which the scanning light bead 16 is instantaneously located. Collecting lenses 43 can also be arranged in front of all the photodetectors to concentrate the light onto the individual photodetectors 14.

In accordance with the invention a beam divider 39 is positioned in the light beam leading to the central photodetector 14d. The beam divider splits the light beam into a part directed to the photodetector 14d and to a part directed to a further photodetector 14d'''. A red filter 44 is inserted in front of the central photodetector 14d and a blue filter in front of the further photodetector 14d'''. The central photodetector 14d thus recognizes the red portion of the white light reaching the beam divider 39 whilst the further photodetector 14d''' recognizes the blue portion. The interconnection of the two photodetectors in the electronic processing circuitry 25 enables the recognition of coloured faults on the surface of the strip 11.

The transmitted light ray which is e.g. generated by a xenon lamp and displaced parallel to itself in the plane of FIG. 2 is designated 46. The cylindrical lens 12 and the cylindrical mirror 13 are arranged at the angle of reflection relative to the transmitted beam 46, in the manner which can be seen from FIG. 2, such that the central beam 46 reflected at the angle of reflection impinges on the two central photocells 14d and 14d''' after reflection at the cylindrical mirror 13.

Beam splitting can also be carried out in the two side channels which can be seen from FIG. 2 by means of beam dividers 39' as is indicated in broken lines in FIG. 2. Whilst the photodetectors 14d' and 14d'' only detect the red portion of the sideways deflected transmitted light due to the insertion of the red filter 44 the two additional detectors 14d'''' and 14''''' are only reached by the blue portion of the sideways deflected transmitted light due to the insertion of the filters 45.

The arrangement of a large number of photodetectors as shown in the embodiment of FIGS. 1 to 3 is economically only justifiable if a large number of different spatial angular ranges is ncessary. In general, and indeed in particular for the recognition of faults on rolled metal surfaces it is, however, sufficient when only a few angular ranges can be distinguished. The embodiment of FIGS. 4 to 6 shows a receiving device which is particularly suitable for the recognition of surface faults on rolled sheet metal.

The receiving device 20 comprises three light conducting rods 17a, 17b, 17c arranged parallel to one another and which are illuminated by received light from cylindrical lenses 18a, 18b, 18c which run parallel to the light conducting rods. The light conducting rods are provided with stepped mirror arrangements 26 at side surfaces diametrically opposite to the light entry side and the stepped mirror arrangements 26 deflect the light in the manner indicated in FIG. 4 at angles of total reflection into the light conducting rod.

In accordance with FIGS. 4 and 5 the light conducting rods 17a and 17c including the associated cylindrical lenses 18a and 18c lie at the same height whilst the central light conducting rod 17b with the associated cylindrical lens 18b is arranged somewhat lower, this has constructional advantages. Because of the displaced arrangement according to FIGS. 4 and 5 it is possible to allow the detection ranges of the three light conducting rods to border directly on one another without the light conducting rods or cylindrical lenses having to be in contact. For longer focal lengths of the cylindrical mirror 13 the displacement of the light conducting rods in the direction of the optical axis does not play any decisive roll.

The light conducting rod arrangement of FIGS. 4 to 6 only makes it possible to distinguish in the first place between three different angular ranges in the plane of FIGS. 2 and 5, this is, however, sufficient for the recognition of dents. The central light conducting rod is illuminated by the light which appears in the focal plane of the cylindrical mirror 13 when the material surface is undamaged. For rolled metal surfaces an extended elongate light bead 27 is used as is schematically illustrated in FIG. 6. The light scattering represented in the light bead 27 originates from the natural striations present in the direction of movement of the strip 11. The elongate light bead 27 produced in this manner illuminates only the central light conducting rod 17b so that the light normally reflected from the undamaged surface of the material strip 11 only illuminates a single photodetector and, indeed, the photodetector 14''''' at the end face of the light conducting rod 17b. The corresponding electrical signal can be used as a reference size for the remaining output signals.

Faulty locations with a significant component transverse to the direction of movement of the strip 11 illuminate the side disposed light conducting rods 17a, 17c and generate corresponding electrical signals at the photodetectors 14''' and 14'''''' provided at the end faces of these light conducting rods.

The beams leaving the strip 11 at the angles α and β fall, in accordance with FIG. 4, on the same light conducting rod 17b as the normal beams so that, in the simplest case, no angular differentiation is carried out in this plane.

In accordance with FIGS. 4 to 6 plane deflecting mirrors 19a, 19c are arranged in the middle of the scanning range above the cylindrical lenses 18a, 18c and the deflecting mirrors deflect incident light outwardly to the photodetectors 14', 14''. The deflecting mirror 19c extends only over a small portion of the length of the light conducting rod 17. Only in this region does it prevent the light deflected from the plane of FIG. 4 from falling on the light conducting rods 17a, 17c.

It has been shown that on the occurrence of depressions or bumps on the material strip 11 which have continuously falling or climbing flanks that the deflection mirrors 19a, 19c are illuminated by the light deflected at these mirrors so that corresponding electrical signals are produced at the photodetectors 14', 14''.

The photodetectors 14' and 14'''''' can be connected to a suitable electronic processing circuitry 25 in analogy to the exemplary embodiment of FIGS. 1 to 3.

As seen in FIG. 6 the central region of the centre light conducting rod 17b of the centre cylindrical lens 18b is covered by a deflecting mirror 19b which in accordance with FIG. 5 projects the light entering the cylindrical lens 12 via a beam divider 39 onto the photodetectors 14h and 14i in front of which a red filter 44 and a blue filter 45 are respectively arranged. In this way two colour channels are once more provided which enable the recognition of coloured faults on the surface of the strip 11.

In place of the centrally arranged deflecting mirror 19h a red filter 44 and a blue filter 45 could also be respectively arranged at the two end faces of the central light conducting rod 17b. A further photodetector 14''''a must in addition be associated with the filter 44. Furthermore, it is necessary that the central light conducting rod 17b scatters the light incident on its surface region to both end faces under angles of total reflection. In this manner the photodetector 14'''' detects the blue portion and the photodetector 14''''a the red portion of the centrally incident transmitted light.

Preferably, however, the reflection of the main light is carried out by the deflecting mirror 19b as in this way colour errors and scratches can be distinguished from each other.

Whilst in accordance with FIG. 5 the reflected main light beam 40 is split into two partial beams 41, 42 the two side disposed central rays can also be split by a beam divider 39', as shown in dotted lines into two distinct colour channels in which filters 44, 45 and two respective photodetectors 14', 14'a and 14'', 14''a are once more respectively arranged. The two colour channels enable the recognition of coloured dent-like raised portions or depressions of the sheet metal surface.

Finally, it is also possible in accordance with the invention to interrupt the central light conducting rod 17b and if necessary also the cylindrical lens 18b in the region of the deflecting mirror 19b, to omit the deflecting mirror 19b and to arrange the detection device 39, 44, 45, 14h, 14i directly behind the space in the light conducting rod. For the complete detection of light from scratches photodetectors, which are connected in parallel, should preferably be provided at both ends of the interrupted light conducting rod 18b.

In place of the colour filters 44, 45 the beam dividers 39, 39' could also be formed as dichroic mirrors. Also every other type of beam division and wave length division can be considered for the purposes of the invention.

FIGS. 7 and 8 show an especially advantageous ray path for the practical realization of the thought underlying the invention in which, for the sake of simplicity, the previously described division of the individual measuring rays into several colour channels is not once more illustrated.

In the exemplary embodiment of FIG. 7, as an alternative to the illuminating optics of FIGS. 1 to 6 the cylindrical mirror 13 and the cylindrical lens 12 are simultaneously used for generating the scanning light bead 16 by using a part of their pupils transverse to the direction of scanning for the transmitted beam 28. A diverging light beam generated via a xenon lamp 24, a condensor 29 and a hole or slot aperture 30 which is made parallel to the front objective 31 is directed via a mirror wheel 22, which is rotatable about an axis 21, onto a plane mirror 23a. The plane mirror 23a projects the transmitted light beam onto the lower region of the cylindrical mirror 13 in FIG. 7. The cylindrical mirror 13 and the cylindrical lens 12 jointly concentrate the light beam on the scanning light bead 16.

Two possibilities are shown in FIG. 7 for housing the receiving device 20. In the one embodiment illustrated in full lines the received beam 32 is directed via the cylindrical mirror 13 onto a plane mirror 23b arranged alongside the plane mirror 23a which, in the illustrated manner, is tilted relative to the plane mirror 23a approximately about an angle at right angles to the plane of FIG. 7. In this way the receiving beam 32 is deflected upwardly so that the receiver device 20 can be arranged at a significant distance from the cylindrical mirror 13 and from the mirror wheel 22.

A simplified embodiment is shown in dotted lines in which only a single plane mirror 23 is provided which receives both beams and which reflects the transmitted light beam 28 to the cylindrical mirror 13 with its lower region whilst the upper region of the plane mirror 23 shown in FIG. 7 deflects the received beam 32 to a receiving device which lies alongside the mirror wheel 22 as seen in the direction of the axis 21. The last named embodiment is characterized by its particularly compact construction.

It is further possible to completely omit the plane mirror 23 and to so arrange the mirror wheel 22 and also the optical elements which illuminate the mirror wheel 22 so that light reflected from the mirror wheel is directly deflected to the cylindrical mirror 13. The receiving device 20 should in this case be likewise arranged alongside the mirror wheel as is shown in broken lines in FIG. 7.

As seen in FIG. 6 stops 34 can also be arranged on both sides of the deflecting mirrors 19a, 19c which have the effect that regions are present in a specified range between the deflecting mirrors 19 and the light conducting rods 17a, 17c in which no light reaches the light conducting rods. In this way a certain angular decoupling is achieved between the light which falls on the deflecting mirrors 19a, 19c and the light which falls on the light conducting rods 17a, 17c. The extent of the stops 34 in the direction of the axis of the light conducting rods corresponds in order of magnitude to the corresponding extent of the deflecting mirror 19.

A transmitter and receiver apparatus which is especially suitable for the recognition of surface faults on sheet metal strips 11 is illustrated in FIG. 8 in the manner in which it is used for the embodiments of FIGS. 1 to 6.

A transmitted beam generated via a xenon lamp 24, a condensor 29, an aperture stop 30 and a front objective 31 is deflected by a mirror wheel 22, which rotates about an axis 21, onto a plane mirror 35 from which it reaches the concave mirror 31' via a further plane mirror 36. The hollow mirror 31' can be formed as a spherical or paraboloid mirror and be of strip form with its axis at right angles to the plane of the drawing. Taking into account the double bending of the beam at the mirrors 35, 36 which in other respects likewise have a strip-like form standing at right angles to the plane of the drawing the concave mirror 31' is spaced from the mirror wheel 22 by a distance equal to its focal length. The transmitted beam 28 is deflected from the concave mirror 31' at an angle ε for creating the scanning light bead 16 on the sheet metal strip 11. The angle ε preferably lies between 10° and 80°. It is important that no further optical elements are present between the concave mirror 31' and the scanning light bead 16. The size of the scanning light bead 16 amounts in this manner to approximately 0.1 by 1 mm to 1 by 10 mm. The distance between the hollow mirror 31' and the scanning light bead 16 lies between ½ and 1/10 of the focal length of the concave mirror 31'.

The cylindrical lens 12 is arranged with its optical axis 33 at the angle of reflection ε of the transmitted beam 28. The light leaving the cylindrical lens is directed via a cylindrical mirror 13 and a plane mirror 23 arranged in accordance with FIG. 8 onto the receiving device 20 which is once more formed in accordance with FIGS. 4 to 6.

As the cylindrical lens 12 is arranged at the angle of reflection ε relative to the transmitted beam 28 the light normally reflected at the surface of the strip 11 practically all reaches the central light conducting rod 18b where, for rolled sheet metal, the pattern 27 of FIG. 6 is generated. The receiving device of FIGS. 4 to 6 is thus preferably arranged at the angle of reflection ε to the transmitted ray 28 in accordance with FIG. 8.

A cylindrical lens 37, behind which is arranged a light conducting rod 38, is located between the transmitted beam 28 and the cylindrical lens 12 practically at right angles to the strip. Both elements extend like the cylindrical lens 12 parallel to the direction of scanning.

The light conducting rod 38 serves to receive the light remitted from the surface of the strip 11. With this detection system stains on the strip surface can preferably be recognized.

The photodetectors used are preferably photo-multipliers.

It will be appreciated that the term cylindrical as applied to the mirrors and lenses used in this application signifies that they are generally of cylindrical curvature and includes other sectional shapes such as parabolic etc.

I claim:

1. Apparatus for determining faults on strip material with a light deflecting device illuminated by an incident light beam to form a scanning light bead on the strip, a cylindrical lens extending over the scanning region and having a focal line extending along the scanning track of the scanning light bead on the strip, a strip-like cylindrical mirror arranged behind the cylindrical lens and spaced therefrom with its focal line extending optically at right angles to the direction of scanning movement of the scanning light bead, and a light receiving device with at least two photodetectors arranged in the focal plane of the cylindrical mirror the said photodetectors to receive light from light beams which leave the strip in different angular ranges with a first one of the photodetectors arranged to receive light leaving the strip at the angle of reflection and wherein by means of filtering, only light in a first spectral range is transmitted to the first photodetector and at least a portion of the beam transmitted to the first photodetector is branched off prior to filtering and, after the filtering out of a second spectral range, is passed to a further photodetector.

2. Apparatus according to claim 1 wherein at least one photodetector is arranged to the side of the first photodetector for receiving light beams deflected transversely to the scanning direction and wherein the at least one photodetector also receives filtered light and at least a portion of the light beam directed to the at least one photodetector is branched off prior to filtering and, after the filtering out of a second spectral range, is passed to an associated photodetector.

3. Apparatus for determining faults on strip material with a light deflecting device illuminated by a light beam to form a scanning light bead on the strip, a cylindrical lens extending over the scanning region and having a focal line extending the scanning track of the scanning light bead on the strip, a strip-like cylindrical mirror arranged behind and spaced from therefrom with its focal line extending optically at right angles to the direction of scanning movement of the scanning light bead and a light detecting device arranged in the focal plane of the cylindrical mirror for receiving light therefrom and having at least two light conducting rods arranged alongside one another parallel to the scanning direction and each having a stepped mirror arrangement on a strip-like surface zone thereof, there being photodetectors provided at end faces of the light conducting rods with one of said light conducting rods being arranged to receive light leaving the strip at the angle of reflection, and wherein the one light conducting rod which is covered at its central region where the light would impinge with an exactly specularly reflecting surface, if necessary taking into account the unavoidable trivial tilting that can occur during transport of the strip, is covered by a stop which is impervious to light.

4. Apparatus according to claim 3 and wherein the stop is a deflecting mirror.

5. Apparatus according to claim 3 and wherein light incident on the stop is deflected to form a deflected light beam with the deflected light beam being divided by wave length into at least two partial beams and wherein each partial beam is passed to a respective photodetector.

6. Apparatus according to claim 3 wherein second and third light conducting rods are respectively disposed one to either side of the one light conducting rod, there being deflecting mirrors arranged in the central regions of the side disposed light conducting rods and means for splitting light beams deflected by the deflecting mirrors by wave length into at least two partial beams with each partial beam being passed to a respective photodetector.

* * * * *